United States Patent
Vora

(10) Patent No.: US 6,590,132 B1
(45) Date of Patent: Jul. 8, 2003

(54) SEPARATION OF MONOMER FROM OLIGOMER WITH LOWER BOTTOMS TEMPERATURE

(75) Inventor: Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/844,208

(22) Filed: Apr. 27, 2001

(51) Int. Cl.⁷ .......... C07C 7/04; C10G 21/20; C10G 7/00; B01D 3/00
(52) U.S. Cl. .......... 585/809; 208/311; 208/313; 208/322; 208/347; 208/348
(58) Field of Search .......... 585/809; 208/311, 208/313, 322, 347, 348

(56) References Cited

U.S. PATENT DOCUMENTS

| | | | |
|---|---|---|---|
| 2,526,966 A | 10/1950 | Oberfell et al. ........ | 196/1 |
| 4,304,948 A | 12/1981 | Vora et al. ........ | 585/315 |
| 4,393,259 A | 7/1983 | Ward et al. ........ | 585/315 |
| 4,749,820 A | 6/1988 | Kuo et al. ........ | 585/330 |
| 5,049,360 A | 9/1991 | Harandi et al. ........ | 422/141 |
| 5,100,515 A | 3/1992 | Lee et al. ........ | 203/56 |
| 5,382,330 A | 1/1995 | Berg ........ | 203/60 |
| 5,877,372 A | 3/1999 | Evans et al. ........ | 585/510 |
| 5,895,830 A | 4/1999 | Stine et al. ........ | 585/259 |
| 5,990,367 A | 11/1999 | Stine et al. ........ | 585/514 |
| 6,025,533 A | 2/2000 | Vora et al. ........ | 585/330 |
| 6,080,903 A | 6/2000 | Stine et al. ........ | 585/514 |

FOREIGN PATENT DOCUMENTS

EP 0 994 088 A1 4/2000

*Primary Examiner*—Walter D. Griffin
*Assistant Examiner*—Tam M. Nguyen
(74) *Attorney, Agent, or Firm*—John G. Tolomei; James C. Paschall

(57) ABSTRACT

The process disclosed separates light olefins from heavy oligomers in a distillation column with an intermediary having a boiling point between the light olefin and the heavy oligomer in the column feed. The invention contemplates separating $C_4$ hydrocarbons from $C_8$ hydrocarbons in an effluent from an oligomerization reactor. The effluent includes or is supplemented with an intermediary that can include $C_5$ hydrocarbon, $C_6$ hydrocarbon or mixtures of both. Consequently, the bottoms reboiler temperature can be lower.

18 Claims, 1 Drawing Sheet

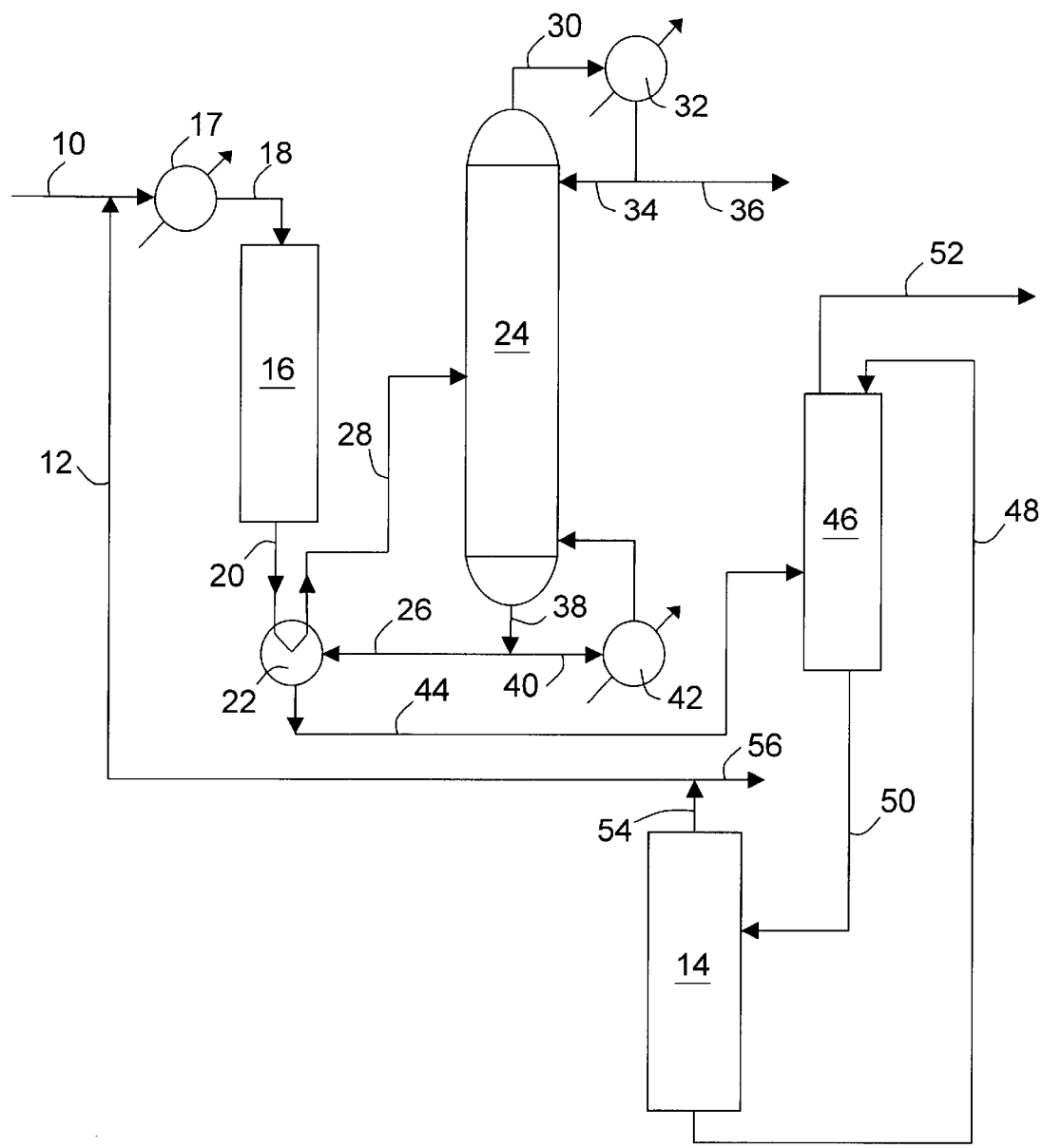

SEPARATION OF MONOMER FROM OLIGOMER WITH LOWER BOTTOMS TEMPERATURE

FIELD OF THE INVENTION

This invention relates to a distillation process for separating $C_4$ olefins from $C_8$ olefins with a bottoms temperature that is lower than what is usually required for effective separation of $C_4$ olefins from $C_8$ olefins.

BACKGROUND OF THE INVENTION

Processes for the oligomerization of light olefins to produce $C_8$ olefin oligomers are known. Oligomerization processes have been long employed to produce high quality motor fuel from $C_4$ olefins. Such oligomerization processes are also referred to as catalytic condensation and polymerization with the resulting motor fuel often referred to as polymer gasoline. Methods have always been sought to improve the $C_8$ olefin number of the gasoline boiling range oligomerization products.

In the oligomerization method of the indirect alkylation process set forth in, for example, U.S. Pat. No. 6,080,903 B1; U.S. Pat. No. 5,990,367 B1 and U.S. Pat. No. 5,895,830 B1, light aliphatic olefins such as $C_4$ olefins are contacted with solid phosphoric acid (SPA) catalyst in the presence of a heavy paraffin diluent such as cyclohexane or octane. The presence of the paraffin diluent is believed to promote the oligomerization in the liquid phase to yield predominantly dimerized oligomers such as $C_8$ olefins. The heavy aliphatic olefins can be saturated to provide high octane fuel. Moreover, light paraffins feed can be dehydrogenated to provide the feed for the indirect alkylation process. Patents disclosing such dehydrogenation include U.S. Pat. No. 4,393,259 B1; U.S. Pat. No. 5,049,360 B1; U.S. Pat. No. 4,749,820 B1; U.S. Pat. No. 4,304,948 B1 and U.S. Pat. No. 2,526,966 B1.

Other oligomerization processes using an ionic exchange resin catalyst to oligomerize light olefins to produce oligomers such as $C_8$ olefins are also known. These processes often include an oxygenate such as tert-butyl alcohol (TBA) or sec-butyl alcohol (SBA) in the feed for modifying the catalyst to maintain desired selectivity. References disclosing resin catalyzed oligomerization include U.S. Pat. No. 5,877,372 B1 and EP 0994088 A1. The resin catalyzed oligomerization can also be preceded by a dehydrogenation zone to convert paraffinic feed into olefinic feed. The oligomerization can also be succeeded by a hydrogenation zone to convert heavy oligomeric olefins into heavy alkanes that can be blended with gasoline stock.

In such oligomerization processes, either before or after hydrogenation, it may be necessary to separate unreacted light olefins from the product heavy oligomers in the effluent from the oligomerization zone. Separation is conventionally performed in a distillation column.

In the distillation column typically after the oligomerization zone the lighter components comprising primarily unreacted light olefins such as $C_4$ olefins and non-participating light alkanes such as $C_4$ alkanes that were present in the feed stream exit from the overhead of the distillation column. The heavier components comprising primarily heavy oligomers such as $C_8$ olefins and smaller amounts of $C_{12}$ olefins along with a heavy paraffinic diluent, if the oligomerization catalyst is SPA, exit out the bottoms of the distillation column. If oxygenate is part of the feed to the oligomerization zone to moderate the resin catalyst instead of paraffinic diluent for SPA catalyst, the oxygenate may go out either or both of the overhead or the bottoms of the column. Because the heavy components such as $C_8$ olefins have a relatively high boiling point temperature which is much higher than the boiling point temperature of the lighter components such as $C_4$ hydrocarbons, the relatively high bottoms temperature of the distillation column will require a higher temperature heat source to boil the contents of the column. For example, if steam is used as a heating medium, steam will have to be delivered at higher pressures to generate the higher temperature. Hence, heating tubes having a sturdier construction are required to handle the higher pressure steam, thereby requiring more complex design and construction costs.

The necessity for the bottoms reboiler of the distillation column to run at a higher temperature is becoming more salient because of recent governmental regulations to decrease or eliminate the use of methyl tert-butyl ether (MTBE) as a gasoline blending component. Many MTBE producers are seeking to convert their MTBE plants to $C_4$ olefin oligomerization plants. MTBE plants generally include a reactor filled with a resin catalyst followed by a distillation column which separates unreacted $C_4$ olefins from MTBE which is brought out the bottoms. The boiling point temperature of MTBE is much less than the boiling point temperature of $C_8$ olefins. Use of an existing $C_4$ olefin/MTBE distillation column for a $C_4/C_8$ olefin distillation column would require a reboiler upgrade so the reboiler could handle the higher temperature operation.

Ways of adding agents to the influent for distillation columns to facilitate separation are known. U.S. Pat. No. 5,100,515 B1 discloses an extractive distillation column which adds a saturated alcohol sulfolane or glycol mixture to an alkane and a close boiling alkene to decrease the volatility of the alkene and facilitate separation. U.S. Pat. No. 5,382,330 B1 discloses adding an agent to a mixture of octane and octene to form an azeotrope between the agent and the octene to decrease the volatility of the octene which is brought out the bottom of the column.

EP 0994088 A1 discloses a distillation column with extra $C_6$ hydrocarbons in the feed stream, but the predominant olefins are $C_5$ olefins, not $C_4$ olefins, and the disclosure does not teach reducing the bottoms temperature.

A creative way of dealing with unreacted butenes from an oligomerization effluent is disclosed in U.S. Pat. No. 6,025,533 B1. This patent discloses a distillation column in an oligomerization process that has a catalytic distillation section for oligomerizing unreacted olefins in the column.

An object of the present invention is to reduce the reboiler temperature needed for separating an oligomer from its unreacted olefin in a distillation column.

A further object of the invention is to reduce the reboiler temperature of a distillation column for separating unreacted $C_4$ components from product $C_8$ components.

SUMMARY OF THE INVENTION

A simple but effective solution for reducing the reboiler temperature required in a distillation column for separating unreacted lighter olefinic components from heavier oligomeric components has been discovered. The solution requires no modification to the column or the reboiler. Instead, an intermediary with a boiling point between those of the light components and the heavy components is added to the feed to the distillation column. For example, if the heavy components are $C_8$ hydrocarbons and the lighter components are $C_4$ hydrocarbons, $C_5$ or $C_6$ hydrocarbons may be used. Typical refiners have many sources of such materials on site. A predetermined amount of such $C_5$ or $C_6$ hydrocarbon intermediary may be supplemented to the oligomerization feed or effluent and be taken out the bottom of the distillation column with the heavy components. All the heavy components will go out the bottom of the distillation column and the distillative separation will then be effected between the $C_4$ components and the $C_5$ and/or $C_6$ components. Accordingly, a higher temperature will not be required of the reboiler in the bottoms of the distillation column. Lastly, most of the added intermediary component would eventually be directed to the gasoline blending pool of a refinery anyway. Hence, the mere diversion of the intermediary through the column will not significantly change the composition of the refinery gasoline pool or substantially add to the cost of operating the unit.

In one embodiment, the present invention relates to a process for separating $C_4$ olefin from $C_8$ olefin by distillation. The process comprises feeding a mixture of $C_4$ olefin and $C_8$ olefin to a distillation column. An intermediary comprising a hydrocarbon having a boiling point that is greater than a boiling point of $C_4$ olefin and less than a boiling point of $C_8$ olefin at the same conditions is fed to the distillation column. An overhead distillate product containing a smaller volume percentage of the $C_8$ olefin and the intermediary and a larger volume percentage of the $C_4$ olefin than contained in the mixture is withdrawn. A bottoms product containing a larger volume percentage of the $C_8$ olefin and the intermediary and a smaller volume percentage of the $C_4$ olefin than contained in the mixture is withdrawn. Lastly, the process is performed with a bottoms temperature that is less than 300° F. (149° C.).

In another embodiment, the present invention relates to a process for separating $C_4$ olefin from $C_8$ olefin by distillation. The process comprises feeding a mixture of the $C_4$ olefin and $C_8$ olefin to a distillation column. An intermediary comprising $C_5$ hydrocarbons is fed to the distillation column. The intermediary has a concentration in the mixture that is less than the concentration of $C_4$ olefin in the mixture. An overhead distillate product containing a smaller volume percentage of the $C_8$ olefin and the intermediary and a larger volume percentage of the $C_4$ olefin than contained in the mixture is withdrawn. A bottoms product containing a larger volume percentage of the $C_8$ olefin and the intermediary and a smaller volume percentage of the $C_4$ olefin than contained in the mixture is also withdrawn.

In a further embodiment, the present invention relates to a process for separating a monomer from an oligomer of the monomer by distillation. The process comprises feeding a mixture of the monomer and the oligomer to a distillation column. $C_4$ olefin is the predominant monomer and $C_8$ olefin is the predominant oligomer. An intermediary comprising a hydrocarbon having a carbon number that is greater than a carbon number of the predominant monomer and less than a carbon number of the predominant oligomer is fed to the distillation column. An overhead distillate product containing a smaller volume percentage of the predominant oligomer and the intermediary and a larger volume percentage of the predominant monomer than contained in the mixture is withdrawn. A bottoms product containing a larger volume percentage of the predominant oligomer and the intermediary and a smaller volume percentage of the predominant monomer than contained in the mixture is also withdrawn.

Additional objects, embodiments and details of this invention can be obtained from the following detailed description of the invention.

BRIEF DESCRIPTION OF THE DRAWING

The FIGURE illustrates a flow scheme for the distillative separation of the present invention.

DETAILED DESCRIPTION OF THE INVENTION

The present invention can be used in the separation of heavier oligomeric components from lighter unreacted olefinic components to reduce the temperature required in the bottoms reboiler as long as there is a sufficiently large spread between the boiling points of both components at the same column conditions. The invention is particularly useful in the production of gasoline by dimerizing $C_4$ olefins to make $C_8$ olefins for a gasoline pool, because an intermediary such as $C_5$ or $C_6$ hydrocarbons can be added to the feed to the distillation column and need not be removed from the heavy components that become part of the gasoline pool. Hence, for illustration purposes, the invention will be described in the context of the dimerization of $C_4$ olefins to make $C_8$ olefins.

In the oligomerization of olefins such as $C_4$ olefins to obtain oligomers such as C8 olefins, the oligomerization effluent stream usually includes light components comprising unreacted $C_4$ olefins along with $C_4$ alkanes and higher components comprising $C_8$ olefins and heavy paraffinic diluent or oxygenate modifier. Hence, the distillation column will have to separate the unreacted light components from the heavy components.

Such distillation columns usually run at pressures of between 75 and 150 psia (517 and 1034 kPa), and to make the separation between $C_4$ hydrocarbons and $C_8$ olefins at those pressures, the bottoms temperature will have to be around 400° F. (204° C.) to obtain the appropriate separation. However, by including $C_5$ or $C_6$ hydrocarbons in the feed going into the distillation column, the bottoms temperature can be lowered substantially.

The $C_5$ and $C_6$ hydrocarbons can be added to the effluent from the oligomerization reactor or can be present with the stream entering the oligomerization reactor. The feed for the oligomerization reactor will typically be a $C_4$ cut from a debutanizing distillation column that follows a fluidized catalytic cracking (FCC) unit. Hence, the debutanizing column can be set to allow a predetermined amount more of $C_5$ hydrocarbons in the $C_4$ cut than is typically desired. The $C_5$ hydrocarbons will proceed into the influent for the oligomerization reactor along with the $C_4$ hydrocarbons. It may be preferable to endeavor to minimize pentenes from the feed so they do not participate in the oligomerization and affect product quality. However, if the feed is supplied from an FCC $C_4$ cut, substantial pentenes will be present in the feed. The $C_4$ olefins for the oligomerization reactor can be provided by another process such as by dehydrogenation of a $C_4$ alkane stream. In such a case, pentanes or hexanes must be provided from another source by addition before or after the oligomerization reactor, but pentenes and hexenes would not be present in the oligomerization reactor to degrade the quality of the oligomerization product.

It will be necessary to run a sufficient quantity of intermediary through the bottoms of the distillation zone to reduce the bottoms temperature. Hence, the feed to the column should have sufficient intermediary to adequately supply the bottoms. The amount of intermediary in the feed will depend on many factors, some of which include the type of intermediary, desired bottoms temperature and acceptable intermediary concentration in the overhead product. However, we believe that the concentration of $C_5$ hydrocarbon intermediary in the feed to the distillation column should be between 2 and 10 wt-%, and preferably between 3 and 7 wt-%. The amount of intermediary in the bottoms of the distillation column will determine the temperature of the reboiler. The amount of intermediary desired in the bottoms of the distillation column will also depend on many factors similar to those listed for determining the amount of intermediary desired in the feed. We believe that the concentration of $C_5$ hydrocarbon intermediary in the bottoms product should be between 10 and 40 wt-%, and preferably between 15 and 30 wt-%.

In the event that an SPA catalyst is used in the oligomerization reactor, it may be preferable to add $C_5$ and especially $C_6$ hydrocarbons to the influent stream to the oligomerization reactor because higher paraffins are believed to promote the oligomerization in the liquid phase to yield predominantly dimerized butene oligomers and to wash deactivating components from the catalyst to promote catalyst life. However, if a resin catalyst, such as a sulfonic acid ion exchange resin, is used in the oligomerization reactor, it may be preferable to add the $C_5$ and/or $C_6$ hydrocarbons to the effluent from the oligomerization reactor before it proceeds to the distillation column. Nevertheless, as previously explained, if the feed is a $C_4$ cut from a debutanizer column following an FCC unit, it is most practical to include the $C_5$ hydrocarbons with the feed going into the oligomerization reactor.

Any suitable reflux ratio can be employed in the distillation column. The reflux ratio is the weight ratio of the portion of condensed vapor which is returned to the distillation column to the portion of condensed vapor which is withdrawn as distillate product. Generally, the reflux ratio is in the range of from about 0.1:1 to about 2:1, and preferably in the range of from about 0.5:1 to about 1.3:1.

Any suitable feed entry location can be selected. Generally, the feed entry location is in the range of from about 2 to about 70 percent of the total height of the column, measured upward from the bottom of the column. Preferably, in the context of the present invention, the feed entry location is in the range of from about 20 to about 60 percent and more preferably in the range of from about 25 to about 50 percent of the total column height.

If it is desired to add the intermediary to the column, separately from the feed, any suitable intermediary entry location may be selected. Generally, the intermediary entry location is preferably in the range of from about 1 to about 49 percent of the total height of the column, i.e., within the bottom half of the column. Because the intent is to remove the intermediary in the bottoms product, removing the intermediary in the bottoms product is made easier by putting fewer trays between the intermediary feed point and the bottom of the column. It is, however, preferred that the intermediary be introduced as a part of the feed mixture.

Any suitable temperature may be employed in the bottoms vessel that contains primarily the heavy components. The temperature is generally at about 300° F. (149° C.) or less. Preferably, the bottoms temperature is at about 280° F. (138° C.) or less. Conversely, if no intermediary is added to the column, the bottoms temperature would be about 395° F. (202° C.). Generally, the overhead temperature of the column where the vapor exits into the condenser is in the range of from about 130° to about 180° F. (54° to 82° C.). Preferably, the overhead temperature is in the range of from about 140° to about 150° F. (60° to 66° C.).

The feed and intermediary may be preheated before they enter the column generally to a temperature close to the column temperature at the corresponding entry point. Any suitable pressure can be employed during the distillation. Generally, the pressure is about 80 to about 150 psia (552 to 1034 kPa), and preferably about 95 to about 135 psia (655 to 931 kPa).

The overhead distillate product withdrawn from the top of the column generally contains a larger volume percentage of the light components than the feed and a smaller volume percentage of the heavy components and intermediary than the feed. A portion of the overhead product may be condensed and refluxed to the top of the column. The overhead product will include some intermediary, such as 1–2 wt-%, but it will predominately comprise the olefin, e.g., $C_4$ olefins. Generally, the bottoms product contains a larger volume percentage of the intermediary and heavy components than the feed, and less of the light components than the feed. A portion of the bottoms product may be reheated and recycled to the lower portion of the column. Furthermore, the bottoms product contains essentially all of the $C_8$ olefins and paraffinic diluent, if SPA is the oligomerization catalyst, because the temperature of the reboiler is much lower than the boiling point of pure oligomer at the column pressure. Moreover, if a resin is the oligomerization catalyst, the column can be run so that essentially all of the oxygenate, at least 95 wt-%, exits the bottom of the column. The $C_5$ or $C_6$ hydrocarbons can be separated from the $C_8$ olefins in the bottoms product by distillation or other suitable separating means and then be recycled back to the distillation column if it is not desirable to release it to the gasoline pool or if supply of $C_5$ and/or $C_6$ hydrocarbons is limited. However, it is more practical to leave the intermediary $C_5$ or $C_6$ hydrocarbons in the bottoms product that is typically blended into gasoline product.

Any suitable total column height and column diameter and number of trays in the distillation column may be employed. The exact dimensions and column designs depend on the scale of the operation, the exact feed composition, the desired recovery and degree of purity of the product, and the like, and can be determined by those having ordinary skill in the art.

An advantage of using the present invention with resin catalyst in the oligomerization reactor is that the $C_5$ or $C_6$ hydrocarbons form an azeotrope with the TBA and SBA which are used as the oxygenate. Hence, if desired, it may be possible to take cuts (not shown) from the distillation column which would remove the azeotrope of the $C_5$ or $C_6$ hydrocarbons and TBA and, perhaps, a separate cut which would remove the $C_5$ or $C_6$ hydrocarbons azeotrope with the SBA.

The invention is disclosed with reference to the FIGURE which shows an oligomerization scheme which uses a resin catalyst in the oligomerization reactor. However, other oligomerization reaction processes can be used in accordance with the separation of the present invention, such as an oligomerization reactor which includes SPA as the catalyst and uses a higher paraffin as a diluent in the reactor.

Feed comprising a $C_4$ hydrocarbon stream from an FCC debutanizer fractionation column that has previously been water washed to remove nitriles and trace amines and statically mixed, which processes are both not shown, is brought into the process via line 10. The $C_4$ hydrocarbon stream typically includes mixed butenes, mixed butanes and $C_5$ hydrocarbon intermediary purposefully released from the debutanizer fractionation column. Tert-butyl alcohol (TBA) and sec-butyl alcohol (SBA) in an azeotropic mixture with water are added to line 10 via line 12 from a stripper column 14. The butyl alcohol and water from line 12 are combined with the feed from line 10 and heated by heater 17. The preheated feed enters the oligomerization reactor 16 via line 18. In the oligomerization reactor 16, the feed contacts a sulfonic ionic exchange resin catalyst, thereby converting the light olefins which are preferably predominantly $C_4$ olefins to oligomers which are preferably predominantly $C_8$ olefins. The oligomerization effluent is carried via line 20 to a heat exchanger 22 where it is heated indirectly from the heat from the bottoms effluent of a distillation column 24 in line 26. Line 28 carries the heated oligomerization effluent into the distillation column 24. Separation is effected in the distillation column 24 between the light components and the intermediary. An overhead stream in line 30 comprising predominantly $C_4$ hydrocarbons, very little intermediary $C_5$ hydrocarbons and very little TBA or SBA is cooled in a condenser 32 and a portion of the condensed overhead is refluxed back to a receiver (not shown) in the distillation column 24 via line 34 while the other portion of the condensed overhead in line 36 is carried to further processing which may include either a direct alkylation unit or preparation for entry into a dehydrogenation unit for further indirect alkylation processing. A bottoms stream in line 38 is split into a first portion which is carried by line 26 for indirect heat exchange with the oligomerization effluent in line 20 in a heat exchanger 22. A second portion of line 38 is brought by line 40 to reboiler 42 where it is heated and is recirculated back to the distillation column 24. Because $C_5$ hydrocarbons are present in the bottoms instead of just $C_8$ hydrocarbons, the reboiler temperature required to boil the mixture of $C_5$ and $C_8$ hydrocarbons in the bottoms is a much lower temperature than would be required to boil pure $C_8$ hydrocarbons. The bottoms stream in line 38 comprises primarily the intermediary $C_5$ hydrocarbons, heavy oligomers including $C_8$ olefins and the TBA and SBA modifier. The unrecycled bottoms stream is carried away by line 44. The unrecycled bottoms product is carried by line 44 to the water wash column 46. In the water wash column 46, a liquid-liquid extraction occurs in which water extracts the water soluble TBA and SBA from the non-water soluble hydrocarbons comprising $C_8$ olefins and $C_5$ hydrocarbons. The water/TBA/SBA stream exits from the bottom of the water wash column 46 via line 50 whereas the product $C_8$ olefins and the intermediary $C_5$ hydrocarbons go out the overhead of the water wash column 46 via line 52 where it is blended with the gasoline pool. When the intermediary is $C_5$ and/or $C_6$ hydrocarbons, it would have typically been blended with the gasoline pool anyway, so the diversion through the inventive process has a minimal effect on the quality of the gasoline blend. The water/TBA/SBA stream is carried through line 50 into stripper column 14. In the stripper column 14, water comes out the bottoms stream 48 for recycle back to the water wash column 46 and the water/TBA/SBA azeotrope is brought out the overhead via line 54 and a portion of the stream in line 54 is recycled back by line 12 to the influent for the oligomerization reactor 16. A portion of the stream in line 54 is transported to further processing by line 56.

EXAMPLE

We conducted a simulation to compare the bottoms temperature of a distillation column for separating $C_4$ from $C_8$ hydrocarbons in which a first feed to the column included no intermediary and a second feed included an intermediary. In the feed that included no intermediary, the simulation indicated that the bottoms product had the properties shown in Table 1.

TABLE 1

| | |
|---|---|
| Overhead Receiver Pressure (psia) | 102.4 |
| Bottoms Product Composition (wt-%): | |
| $C_4$ Hydrocarbons | 0.15 |
| TBA and SBA | 4.1 |
| $C_8$ Hydrocarbons | 78.7 |
| Other Products | 12.8 |
| Bottoms Temperature (° F.) | 395 |

The second feed was simulated to include 4350.5 lb/hr (1975.1 kg/hr) of intermediary $C_5$ hydrocarbons in the feed and the column was simulated to run with 27 wt-% of $C_5$ hydrocarbons in the bottoms product and 72% of the $C_5$ hydrocarbons fed to the column coming out in the bottoms product. The bottoms product had the properties shown in Table 2.

TABLE 2

| | |
|---|---|
| Overhead Receiver Pressure (psia) | 125.0 |
| Bottoms Product Composition (wt-%): | |
| $C_4$ Hydrocarbons | 0.7 |
| TBA and SBA | 3.7 |
| $C_8$ Hydrocarbons | 59.0 |
| $C_5$ Hydrocarbons | 27.0 |
| Other Products | 9.3 |
| Bottoms Temperature (° F.) | 269 |

The addition of $C_5$ hydrocarbons to the feed resulted in a reduction in the bottoms temperature of 126° F. (70° C.). Moreover, in debutanizing columns used for separating unreacted butene from MTBE product in a MTBE plant, a typical bottoms temperature at the same column overhead receiver pressure is about 269° F. (132° C.). Accordingly, by adding $C_5$ hydrocarbons to the feed going into the distillation column, the same distillation column previously used in an MTBE plant can be used without equipment modifications to the reboiler configuration in a $C_4$ olefin oligomerization plant.

What is claimed is:

1. A process for separating $C_4$ olefin from $C_8$ olefin by distillation comprising:
    a) feeding a mixture of $C_4$ olefin and $C_8$ olefin to a distillation column;
    b) feeding an intermediary comprising a hydrocarbon having a boiling point that is greater than a boiling point of $C_4$ olefin and less than a boiling point of $C_8$ olefin at the same conditions to the distillation column, said intermediary comprising between 2 and 10 wt-% of all feed to the distillation column;
    c) withdrawing an overhead distillate product containing a smaller volume percentage of said $C_8$ olefin and said intermediary and a larger volume percentage of said $C_4$ olefin than contained in said mixture; and
    d) withdrawing a bottoms product containing a larger volume percentage of said $C_8$ olefin and said intermediary and a smaller volume percentage of said $C_4$ olefin than contained in said mixture, a bottoms temperature in the bottoms of the distillation column being less than 300° F.

2. The process of claim 1 wherein the intermediary is a $C_5$ hydrocarbon.

3. The process of claim 1 wherein a $C_4$ alkane is present in the mixture and a greater volume percentage of the $C_4$ alkane is present in the overhead distillate product than in said mixture.

4. The process of claim 1 wherein an oxygenate is present in the mixture and a greater volume percentage of the oxygenate is present in the bottoms product than in said mixture.

5. The process of claim 1 wherein the intermediary is selected from the group consisting of $C_5$ and $C_6$ hydrocarbons.

6. The process of claim 1 wherein a paraffin having a carbon number greater than five is present in the mixture and a greater volume percentage of the paraffin is present in the bottoms product than in said mixture.

7. The process of claim 1 which is preceded by an oligomerization reaction in which $C_4$ olefin oligomerizes to produce the $C_8$ olefin in the mixture.

8. The process of claim 4 wherein at least 95 wt-% of said oxygenate goes out in said bottoms product.

9. A process for separating $C_4$ olefin from $C_8$ olefin by distillation comprising:
   a) feeding the $C_4$ olefin and C8 olefin to a distillation column;
   b) feeding an intermediary comprising $C_5$ hydrocarbons and an oxygenate to the distillation column to provide a mixture of $C_4$ olefin, $C_5$ hydrocarbons, $C_8$ olefin and oxygenate, said intermediary having a concentration of between 2 and 10 wt-% of the mixture which is less than the concentration of $C_4$ olefin in the mixture;
   c) withdrawing an overhead distillate product containing a smaller volume percentage of said $C_8$ olefin and said intermediary and a larger volume percentage of said $C_4$ olefin than contained in said mixture; and
   d) withdrawing a bottoms product containing a larger volume percentage of said $C_8$ olefin, said oxygenate and said intermediary and a smaller volume percentage of said $C_4$ olefin than contained in said mixture.

10. The process of claim 9 wherein $C_4$ alkane is present in the mixture and a greater volumen percentage of the $C_4$ alkane is present in the overhead distillate product than in said mixture.

11. The process of claim 9 wherein at least 95 wt-% of the oxygenate goes out in the bottoms product.

12. The process of claim 9 wherein a paraffin having a carbon number greater than five is present in the mixture and a greater volume percentage of the paraffin is present in the bottoms product than in said mixture.

13. The process of claim 9 which is preceded by an oligomerization reaction in which $C_4$ olefin oligomerizes to produce the $C_8$ olefin fed to the distillation colum.

14. The process of claim 9 wherein a bottoms product comprises at least 15 wt-% intermediary.

15. The process of claim 9 wherein a bottoms temperature is less than 300° F. on average.

16. A process for separating a monomer from an oligomer of the monomer by distillation comprising:
   a) feeding a mixture of the monomer and the oligomer to a distillation column, $C_4$ olefin being a predominant monomer and $C_8$ olefin being a predominant oligomer;
   b) feeding an intermediary comprising a hydrocarbon having a carbon number that is greater than a carbon number of the predominant monomer and less than a carbon number of the predominant oligomer to the distillation column, said intermediary comprising between 2 and 10 wt-% of all feed to the distillation column;
   c) withdrawing an overhead distillate product containing a smaller volume percentage of said predominant oligomer and said intermediary and a larger volume percentage of said predominant monomer than contained in said mixture,; and
   d) withdrawing a bottoms product containing a larger volume percentage of said predominant oligomer and said intermediary and a smaller volume percentage of said predominant monomer than contained in said mixture, wherein a temperature in the bottoms of the distillation column is less than 300° F. on average.

17. The process of claim 16 wherein the intermediary comprises $C_5$ hydrocarbon.

18. A The process of claim 16 wherein a bottoms product comprises at least 15 wt-% intermediary.

* * * * *

UNITED STATES PATENT AND TRADEMARK OFFICE
CERTIFICATE OF CORRECTION

PATENT NO. : 6,590,132 B1  
DATED : July 8, 2003  
INVENTOR(S) : Bipin V. Vora

It is certified that error appears in the above-identified patent and that said Letters Patent is hereby corrected as shown below:

<u>Column 8,</u>  
Line 59, replace "a bottoms temperature" with -- a temperature --.

Signed and Sealed this

Seventh Day of October, 2003

JAMES E. ROGAN  
*Director of the United States Patent and Trademark Office*